(12) United States Patent
Addison et al.

(10) Patent No.: US 7,171,269 B1
(45) Date of Patent: Jan. 30, 2007

(54) METHOD OF ANALYSIS OF MEDICAL SIGNALS

(75) Inventors: Paul Stanley Addison, Edinburgh (GB); James Nicholas Watson, Edinburgh (GB)

(73) Assignee: Cardiodigital Limited, East Lothian (GB)

( * ) Notice: Subject to any disclaimer, the term of this patent is extended or adjusted under 35 U.S.C. 154(b) by 0 days.

(21) Appl. No.: 09/980,770

(22) PCT Filed: May 2, 2000

(86) PCT No.: PCT/GB00/01675

§ 371 (c)(1),
(2), (4) Date: Nov. 1, 2001

(87) PCT Pub. No.: WO01/82099

PCT Pub. Date: Nov. 1, 2001

(30) Foreign Application Priority Data

| May 1, 1999 | (GB) | 9910019.0 |
| Jul. 15, 1999 | (GB) | 9916499.8 |
| Aug. 20, 1999 | (GB) | 9919677.6 |
| Oct. 1, 1999 | (GB) | 9923110.2 |
| Feb. 17, 2000 | (GB) | 0003711.9 |

(51) Int. Cl.
*A61N 1/18* (2006.01)

(52) U.S. Cl. ............ 607/7; 607/4; 607/5; 607/6; 607/8; 607/142; 607/143; 600/407; 600/506; 600/509; 600/521; 600/522; 600/523; 128/901; 128/902; 378/98.5

(58) Field of Classification Search ............... 600/508, 600/504, 513
See application file for complete search history.

(56) References Cited

U.S. PATENT DOCUMENTS

| 5,020,540 A | * | 6/1991 | Chamoun | 600/509 |
| 5,077,667 A | | 12/1991 | Brown et al. | |
| 5,348,020 A | * | 9/1994 | Hutson | 600/509 |
| 5,439,483 A | | 8/1995 | Duong-Van | |
| 5,474,078 A | * | 12/1995 | Hutson | 600/512 |
| 5,531,776 A | * | 7/1996 | Ward et al. | 607/105 |
| 5,571,142 A | * | 11/1996 | Brown et al. | 607/5 |
| 5,772,613 A | * | 6/1998 | Gelfand et al. | 601/41 |
| 5,778,881 A | * | 7/1998 | Sun et al. | 600/509 |
| 5,795,304 A | | 8/1998 | Sun et al. | |
| 5,827,195 A | * | 10/1998 | Lander | 600/509 |
| 5,938,594 A | * | 8/1999 | Poon et al. | 600/300 |
| 5,967,995 A | * | 10/1999 | Shusterman et al. | 600/516 |
| 5,997,488 A | * | 12/1999 | Gelfand et al. | 601/41 |
| 5,999,852 A | * | 12/1999 | Elabbady et al. | 607/8 |
| 6,070,098 A | * | 5/2000 | Moore-Ede et al. | 600/544 |
| 6,171,257 B1 | | 1/2001 | Weil et al. | |
| 2002/0016293 A1 | * | 2/2002 | Ratain et al. | 514/9 |

(Continued)

FOREIGN PATENT DOCUMENTS

WO   WO 96 08992 A   3/1996

OTHER PUBLICATIONS

Millet-Roig, J., et al., Database Inspec [Online] Institute of Electrical Engineers, Stevenage, GB, Sep. 13, 1998, XP002145546.
Chen, J., et al., IEICE Transactions on Information and Systems, JP, Institute of Electronics Information and Comm., Eng. Tokyo, E76-D (12): 1454-1461 (1993).
Geva, A.B., Database Inspec [Online] Institute of Electrical Engineers, Stevenage, GB; Nov. 5, 1996, XP002145547.
Sava, H., et al., Medical and Biological Engineering and Computing, GB, Peter Peregrinus Ltd. Stevenage, 36 (3) 302-308 (1998).

* cited by examiner

*Primary Examiner*—Brian L. Casler
*Assistant Examiner*—William Jung
(74) *Attorney, Agent, or Firm*—Nixon Peabody LLP

(57) ABSTRACT

A method of analysis of medical signals which uses wavelet transform analysis to decompose cardiac signals. Apparatus for carrying out the method, and cardiac apparatus adapted to employ the method are also described.

18 Claims, 14 Drawing Sheets

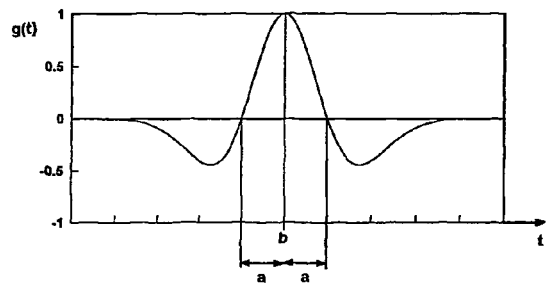
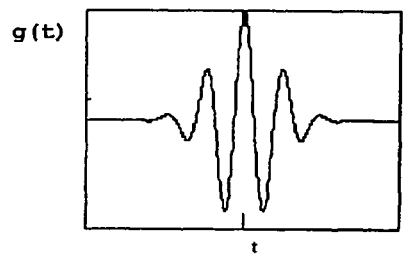
Figure 1(a)　　　　　　Figure 1(b)
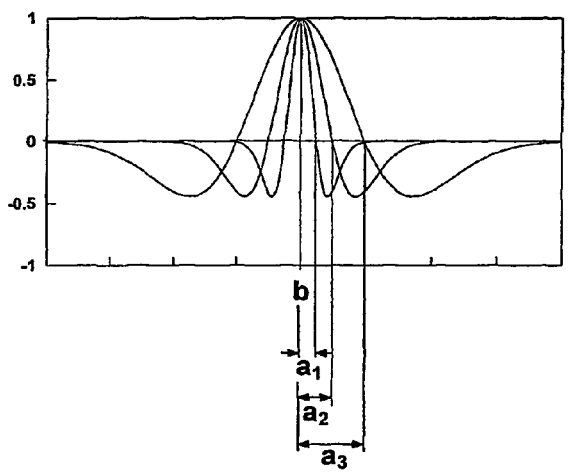
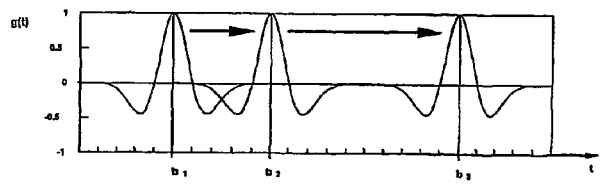
Figure 2(a)　　　　　　Figure 2(b)

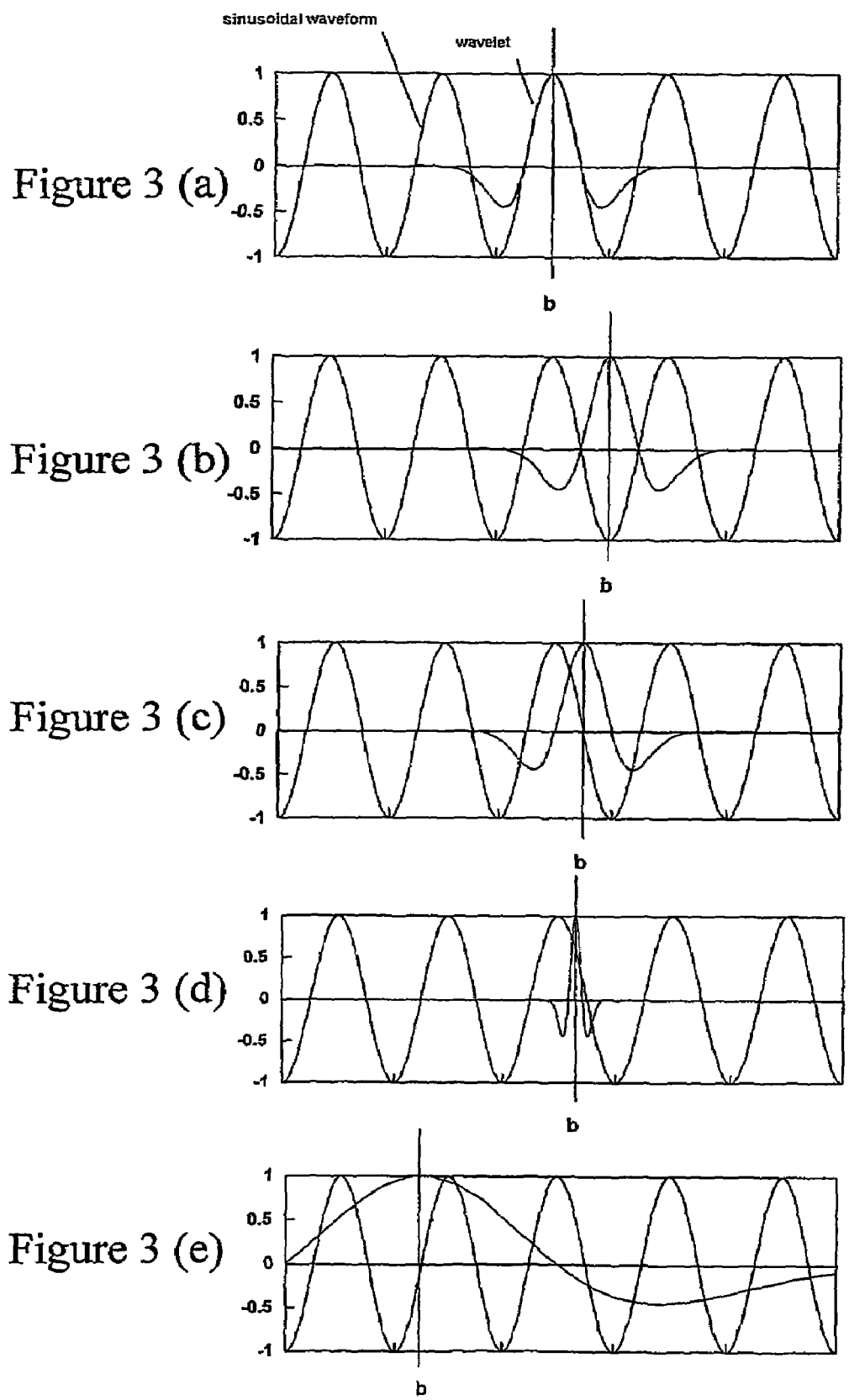

1.9 Hz            9.3 Hz mean energy (log)

Time (Seconds)

Original signal

QRS and T Filtered

QRS and T signal

METHOD OF ANALYSIS OF MEDICAL SIGNALS

This invention relates to a method of analysis of medical signals, and in particular to a method of decomposition of cardiac signals using wavelet transform analysis. Specifically the invention relates to an improved method of resuscitation of patients in cardiac arrest.

In the UK, coronary heart disease is the second greatest contributor to deaths of people under 75. The social and economic consequences of these death rates are enormous. The current survivability rates of patients after sudden cardiac failure are around 1:10.

Ventricular tachyarrhythmias, specifically ventricular fibrillation (VF), are the primary arrhythmic events in cases of sudden cardiac death. Administration of prompt therapy to a patient presenting with such symptoms can however lead to their successful resuscitation. Until recently, the only indicators of likelihood of survival of a patient to hospital discharge were traditional variables such as emergency service response time or bystander cardiopulmonary resuscitation (CPR).

In most cardiac complaints, analysis of a surface electrocardiogram (EKG) of the presenting patient is a rich source of information. However, until recently, a surface EKG recorded during VF and any subsequent medical intervention to defibrillate, was thought merely to present unstructured electrical activity, and not to provide useful information.

The first attempts to derive prognostic information from EKGs of the heart in VF focussed on the importance of the amplitude of the waveform defined using peak-to-trough differences in the EKG voltage, measured as either the greatest deflection occurring in a predefined time slot, or as the average peak-to-trough voltage measured over a given time interval. It has been shown that the VF amplitude is inversely related to time elapsed since collapse, is a crude predictor of defibrillation outcome, and is a better indicator of survival to hospital discharge than the traditional variables described above.

However, recording the VF amplitude accurately is significantly problematical. The EKG voltage amplitude measured during VF is dependent on the direction of the main fibrillation vector and is influenced by a variety of factors including patient chest shape; electrode size; electrode location; and skin/electrode interface resistance. This number of variables makes this amplitude measure both unreliable and inaccurate. That is, although the amplitude of the waveform of an EKG recorded during VF is now recognised to be a crude predictor of the likely outcome of resuscitation of a patient in VF, it is not a reproducible marker of sensitivity to defibrillation, and lacks clinical usefulness.

In a further development, it is also known to use Fast-Fourier based transforms to generate a frequency spectrum of an EKG in VF to analyse the signal. The median frequency (MF) divides the area under the spectrum into two equal parts. Since this plot is derived from information in both the voltage and time domains, external variables such as lead placement have less effect on the results than the method of observing the amplitude. However, CPR produces artefacts in the recorded EKG signal and, since pausing CPR merely to obtain an EKG signal free of artefacts is likely to compromise resuscitation, these artefacts are necessarily included in this frequency measure, and detract from its usefulness.

Thus the results of such signal analysis show some correlation with the likely outcome of resuscitation, but again lack sufficient sensitivity and specificity for clinical use. That is, this form of analysis has the disadvantage that, since the Fourier spectrum contains only globally averaged information, specific features in the signal are lost.

A method of accurate analysis of a surface EKG waveform recorded during VF would therefore be useful in understanding the pathophysiological processes in sudden cardiac death, and thus to produce a model for use:

in predicting the efficacy of therapy in individual cases; and in determining the selection of the preferred course of primary, and alternative or adjunct therapies thus providing a means for individually tailored therapy for the specific patient needs to improve the success rate of resuscitation of patients presenting in VF.

Atrial fibrillation (AF) is a common cardiac arrhythmia in older people. Atrial fibrillation can be stopped by giving an electric shock to the patient under general anaesthetic (cardioversion). However, many patient return to an AF rhythm soon after treatment. The technology detailed here may also provide a tool to facilitate the clinical evaluation of AF exhibited in the electrocardiogram (EKG) so reducing the risk associated with general anaesthetic in patients where the applied therapy is likely to prove ineffective.

According to the present invention there is provided a method of decomposition of waveforms in a cardiac signal using wavelet transform analysis.

The method of the invention is non-invasive, accurate, and capable of delivering real-time information.

Preferably said method employs discretized wavelet transform analysis to process the EKG.

Preferably said method employs discretized continuous wavelet transform analysis to process the EKG.

Preferably said method comprises the steps of deriving the wavelet energy surfaces of an EKG signal; and plotting said wavelet energy surfaces against a location parameter b, and a scale parameter. The scale parameter may be dilation a or band pass frequency $f_{bpc}$.

The method initially comprises the steps of connecting electrodes to the presenting patient; and sampling the analogue input signal to derive the cardiac signal.

Typically said method comprises the step of visually displaying the cardiac signal.

Said method may display the distribution of energies within the cardiac signal. Said method may display coherent structures within the cardiac signal.

Said display may be by means of a contour plot. Said display may be by means of a surface plot. Preferably said method provides means to visualise the signal in real-time for clinical use.

Preferably said method is applicable in the analysis of an EKG in ventricular fibrillation.

Said method may be applicable in the analysis of an EKG in ventricular fibrillation after the commencement of cardiopulmonary resuscitation (CPR).

The method may include the step of disassociating the component features of the temporal trace of a recorded EKG. Additionally or alternatively said method may include the step of temporal filtering of an EKG signal of a heart which is subject to CPR to disassociate the CPR signal from the heart signal.

Typically said method provides measurable characteristics for the estimation of the health of a heart in VF. Said method may provide measurable characteristics for the estimation of the health of a heart in AF. Said me may provide Typically said method provides measurable characteristics for the estimation of the health of a heart.

The method may provide measurable characteristics for the estimation of the time elapsed since the onset of a cardiac incident.

Typically said method provides measurable characteristics for the estimation of the health of a heart after commencement in CPR.

Said method may provide a prediction for the outcome of a given therapeutic intervention and so aid the clinical decision making process.

Said method may provide a basis for individual, patient specific, protocols for therapeutic intervention.

The method may provide a guide to the optimal timing of defibrillation of a heart in VF.

Said method may include the step of constructing a damage index for reference purposes. Construction of said index might involve the development of a network classifier from a library of recorded data. Said network classifier may comprise a neural network. Said network classifier may comprise a wavelet network classifier.

Application of the method of the invention represents a significant advance in coronary care by providing a reliable predictor of the outcome of shocking a patient in VF. In addition, the development of an algorithm using the method of the invention gives the ability to predict shock outcome and to facilitate individual patient therapy. The ability to provide patient specific therapeutic intervention is a priority in the advancement of currently applied medical protocols.

That is, as discussed above, in certain instances, after prolonged cardiac arrest preceding defibrillation pharmacological measures or CPR can increase the chance of successful resuscitation. Thus, employing the method to predict the outcome of shocking avoids futile defibrillation attempts which can even harm the heart, and can indicate the need for intervention, and influence the selection of the preferred type of intervention, to optimise the metabolic state of the heart prior to counter-shock.

The predictor algorithm developed using the method is being tested using a new generation of defibrillation devices that have the flexibility to allow easy prototyping of the new defibrillation algorithms.

According to a further aspect of the present invention there is provided a method of decomposition of waveforms in a cardiac signal using matching pursuit algorithms.

According to a further aspect of the present invention there is provided an apparatus for decomposition of waveforms in a cardiac signal, said apparatus comprising wavelet transform analysis means.

Said apparatus may include means to display the distribution of energies within a waveform.

Said apparatus may include a monitor adapted to display decomposed waveforms. Said apparatus may be adapted for inclusion in an EKG apparatus.

According to a further aspect of the present invention there is provided defibrillation means adapted to operate in response to a signal generated by comparison of an EKG trace with decomposed waveform.

That is, the invention preferably provides a method of wavelet analysis of cardiac signals which provides structural information about the heart—whether the heart is healthy or not—and has significant advantages over fast Fourier transforms.

The invention may provide a display device in the form of a scrologram that provides real-time visualisation of a wavelet scalogram, showing the distribution of energies and coherent structures within the signal for use as guidance by a clinician.

The invention may further provide a data analysis tool, which assists in shock timing (atrial pulsing). That is, the derived data may indicate the optimum time to administer shock to the heart. The invention may provide a damage index, preferably in the form of an artificial neural network.

Preferably the invention provides dissociation of the component features of a temporal trace of a cardiac signal, which may for example be CPR, AF, or cardio-phonographic signals.

Embodiments of the invention will now be described by way of example only and with reference to the accompanying drawings in which:

FIG. 1a is a Mexican hat wavelet;

FIG. 1b is the real part of a complex Morlet wavelet;

FIG. 2a is a schematic plot showing the dilation of a continuous wavelet;

FIG. 2b is a schematic plot showing the translation of a continuous wavelet;

FIG. 3a to FIG. 3e are the plots of the 'investigation' of a sinusoidal signal by Mexican hat wavelets of various sizes, showing the effect of translation of the wavelet along the signal (change in b), and dilation of the wavelet (change in a);

FIG. 4a is the plot of five cycles of a sine wave of period P;

FIG. 4b is the contour plot of T(a,b) against a and b for the sine wave of FIG. 4a;

FIG. 4c is the isometric surface plot of T(a,b) against a and b for the sine wave of FIG. 4a;

FIG. 5a is the plot of a combination of two sine waves of period P1, and P2, where P1=5P2;

FIG. 5b is the contour plot of T(a,b) against a and b for the sine wave of FIG. 5a;

FIG. 5c is the isometric surface plot of T(a,b) against a and b for the sine wave of FIG. 5a;

FIG. 6a is an EKG trace of a pig heart in sinus rhythm;

FIG. 6b is a 2D energy scalogram associated with the EKG trace of FIG. 6a;

FIG. 6c is a 3D energy scalogram associated with the EKG trace of FIG. 6a;

FIGS. 6d, 6e, 6f and 6g are the energy surface plots from four segments of an EKG signal subsequent to the onset of VF, showing the three dominant ridges A, B, and C appearing in the transform surface, and showing in FIG. 6g the onset of CPR after five minutes, associated with a gradual increase in passband frequency of the ridges A, B, and C;

FIG. 7a is an energy scalogram for a pig heart for the first seven minutes of ventricular fibrillation, indicating the initiation of CPR after five minutes;

FIG. 7b is a schematic diagram of the salient features of the scalogram of FIG. 7a;

FIG. 7c is the smoothed plot of energy at the 8 Hz level in the scalogram of FIG. 7a against time;

Figure 8:
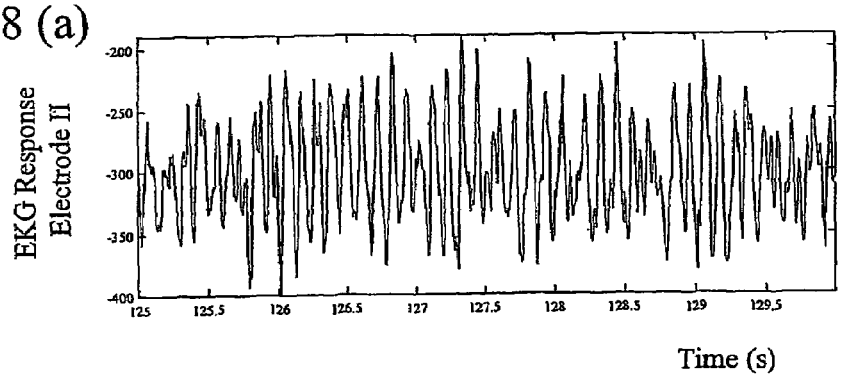
FIG. 8a is a typical segment of an EKG trace of a pig heart in VF.
Figure 8:
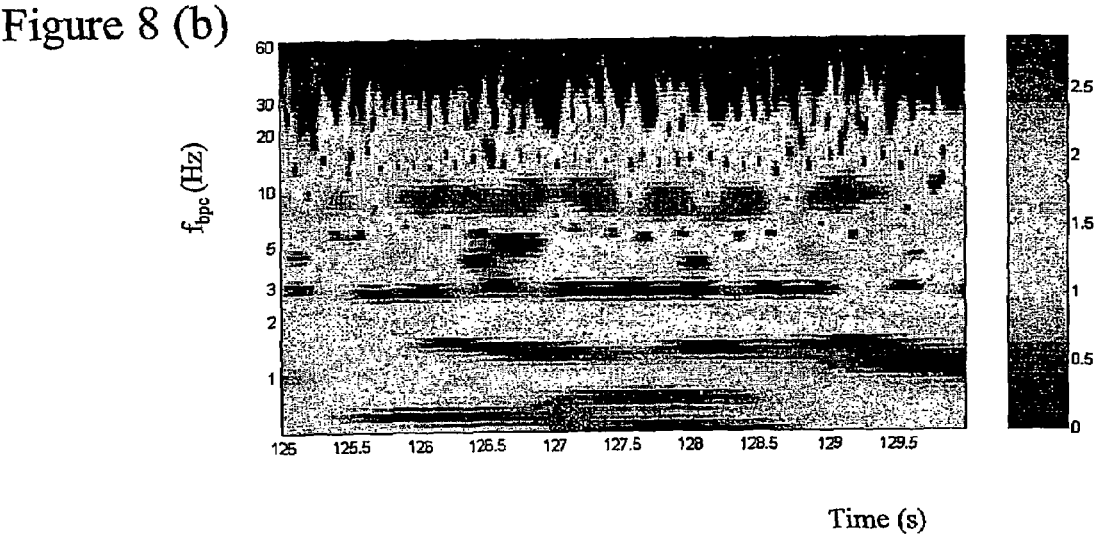
Figure 8:
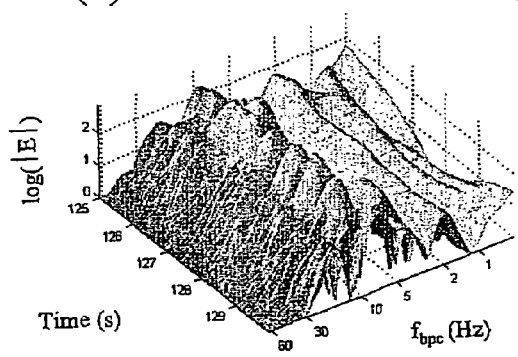
Figure 8:
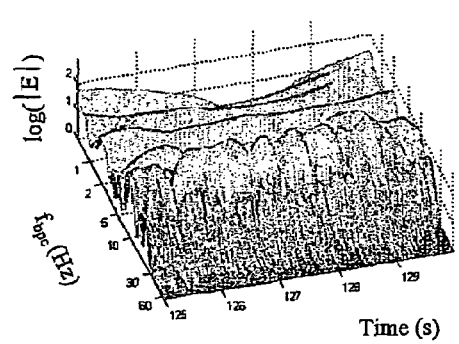
Figure 9:
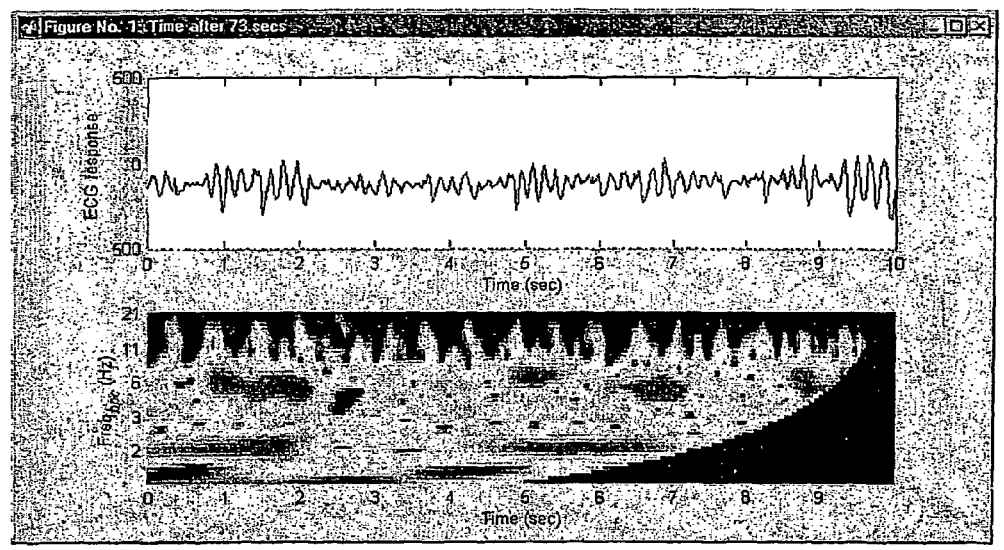
Figure 10:
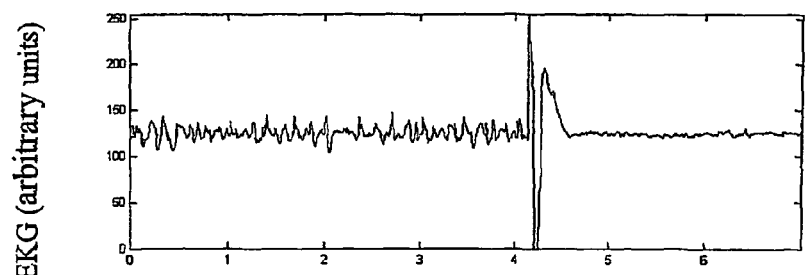
Figure 10:
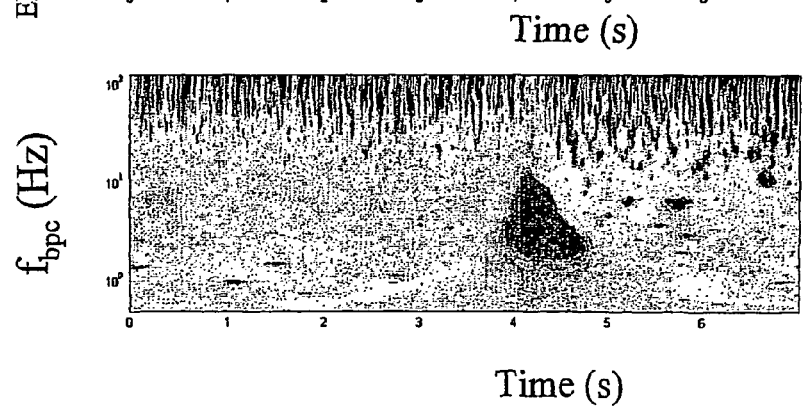
Figure 12:
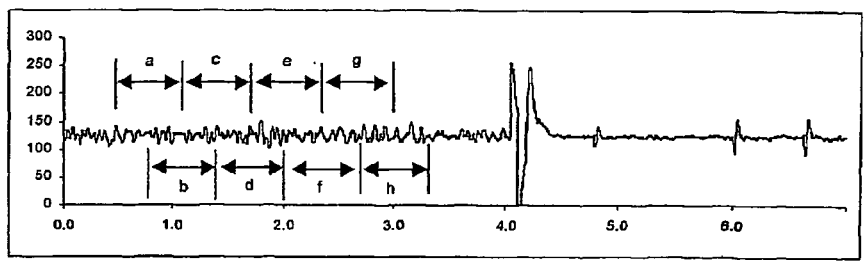
Figure 12:
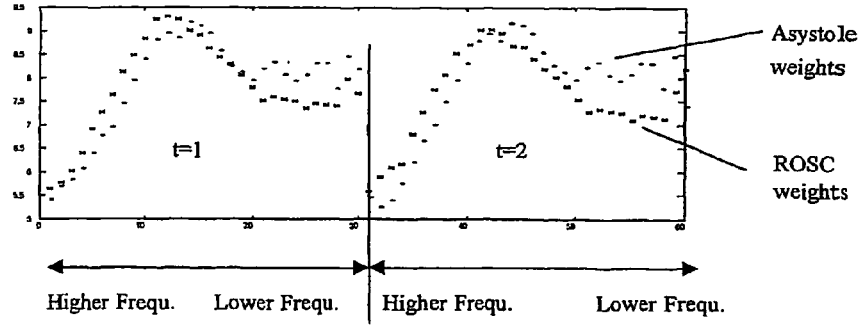
Figure 13:
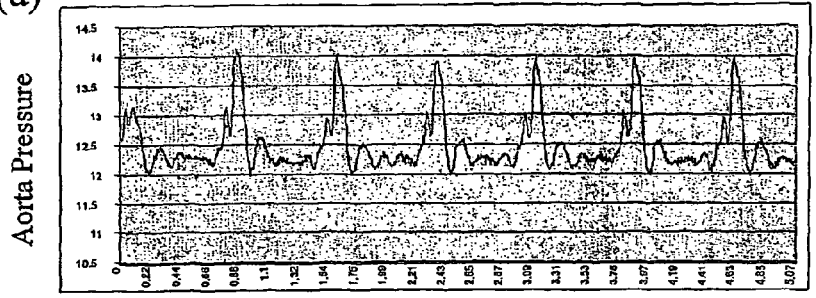
Figure 13:
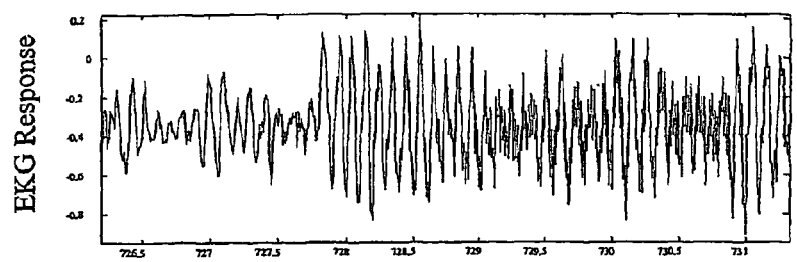
Figure 13:
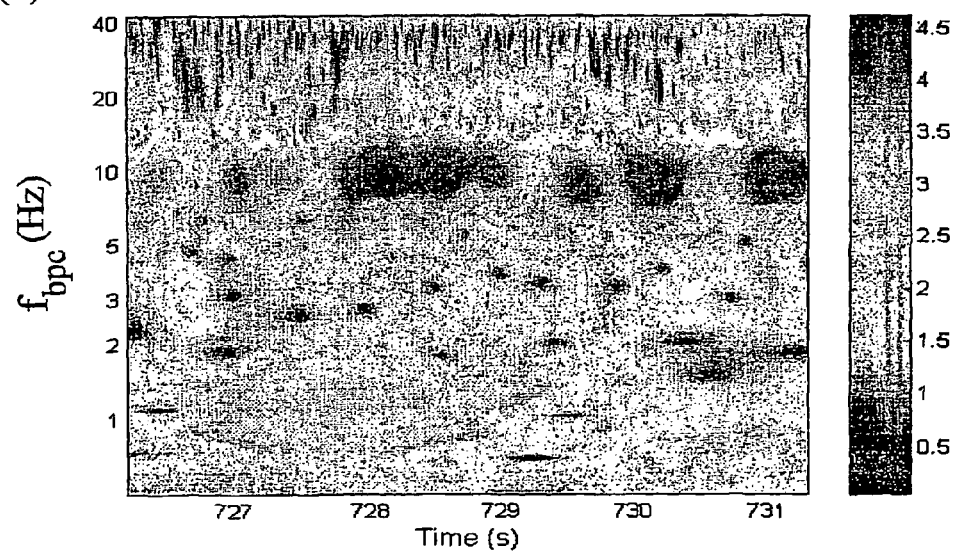
Figure 13:
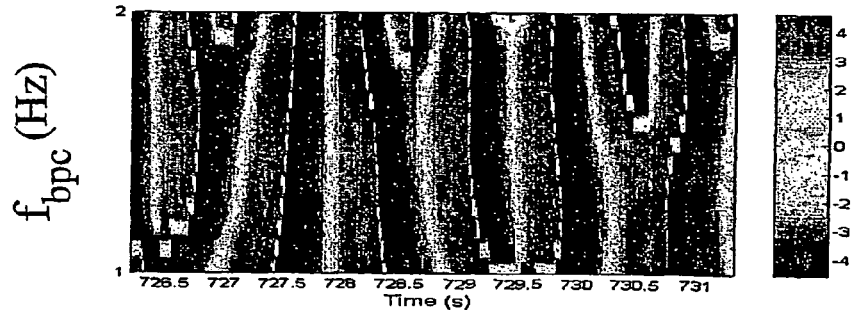
Figure 13:
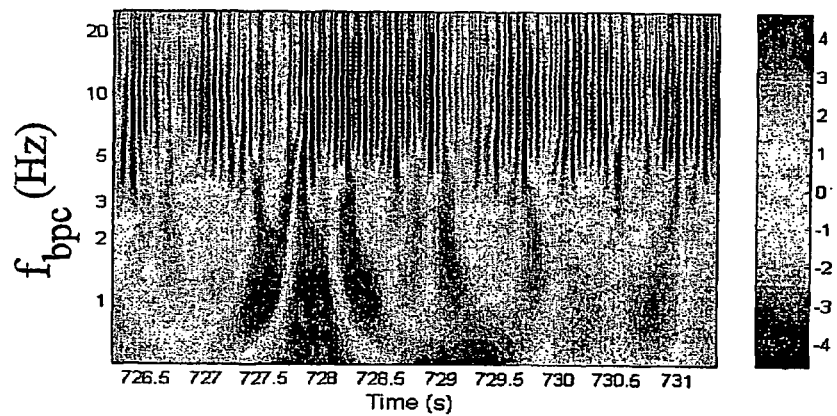
Figure 13:
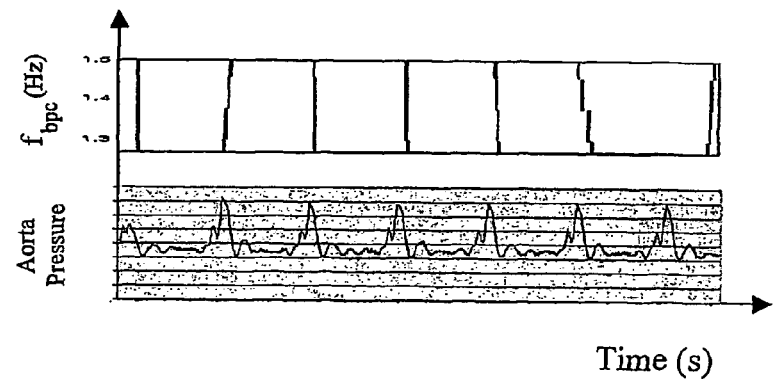

FIGS. 8b, 8c, and 8d are the energy scalograms associated with the trace of FIG. 8a;

FIG. 9 is a screen shot of a real time viewer which shows the collected EKG data with its associated wavelet energy display in the form of its energy scalogram, where windows scroll to the right;

FIG. 10a is a 7 second trace of human ECG showing a shock event;

FIG. 10b is a scalogram corresponding to the trace of FIG. 10a;

FIG. 11a shows the proportion of energy in scalograms for 120 results (60 ROSC, and 60 asystole) at 1.9 Hz after shocking;

FIG. 11b shows the proportion of energy in scalograms for 120 results (60 ROSC, and 60 asystole) at 9.3 Hz after shocking;

FIG. 12a is a schematic representation of overlapping signal segments used in a neural network test study;

FIG. 12b shows the weights attributed by the Kohonen network to the 30 frequency levels used in the scalogram;

FIG. 13a is an aorta pressure trace;

FIG. 13b shows the EKG for the same time period as the trace of FIG. 13a; and

Figure 14:
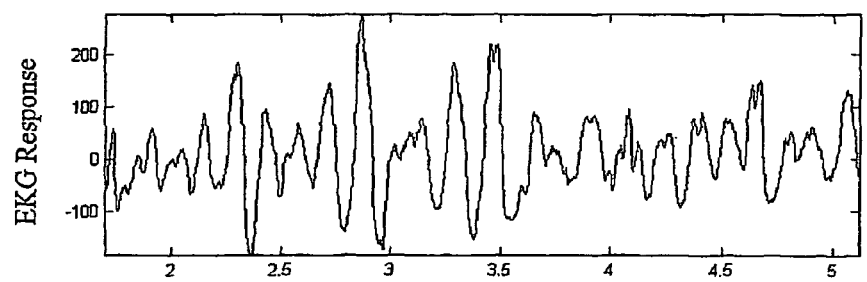
Figure 14:
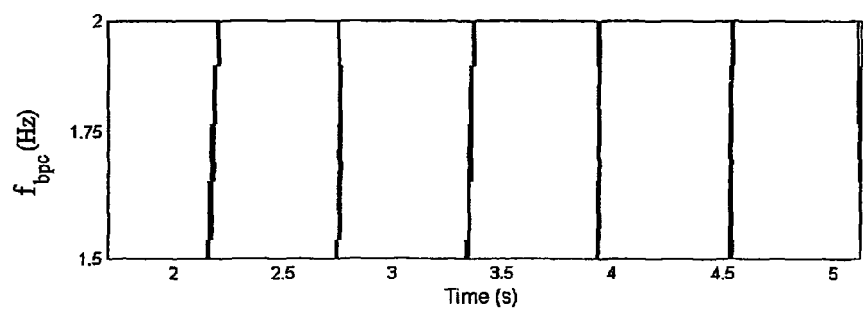
Figure 14:
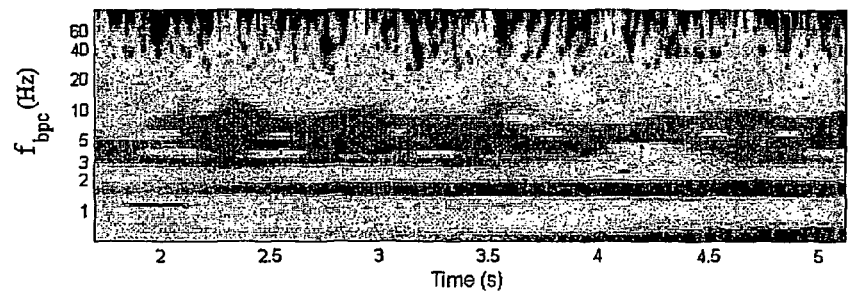

FIG. 13c is the scalogram associated with the trace of FIG. 13a derived from the Morlet wavelet;

FIG. 13d is a detail of the phase part of scalogram FIG. 13c;

FIG. 13e is the scalogram associated with the trace of FIG. 13a derived from the Mexican hat wavelet; and FIG. 13f demonstrates the correlation of aorta pressure pulse position with lines of zero phase;

FIG. 14a is the plot of an EKG trace. FIG. 14b is its associated phase at around 1.5 Hz. FIG. 14c is its energy scalogram. The correlation of zero phase at this lower frequency and high frequency (low dilation) peaks is thus illustrated.

Figure 15:
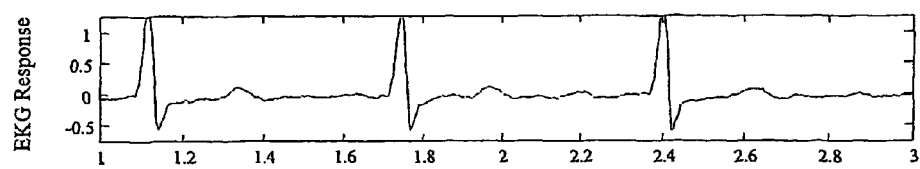
Figure 15:
Figure 15:
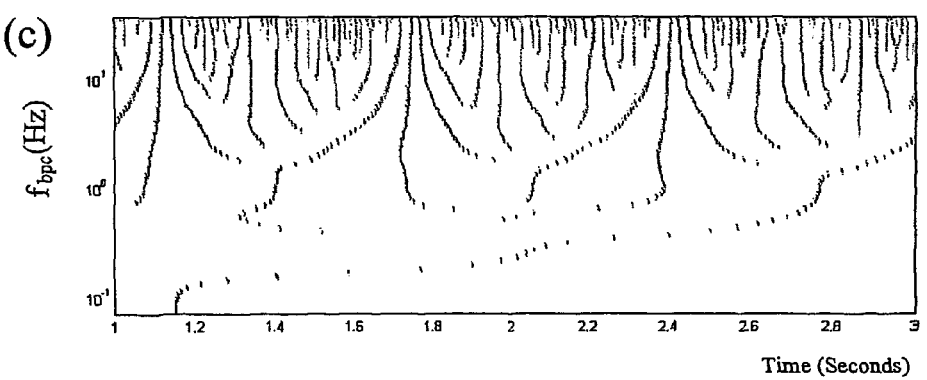
Figure 15:
Figure 15:
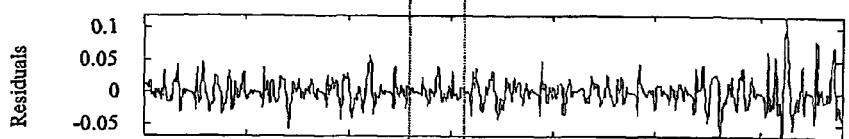
Figure 15:
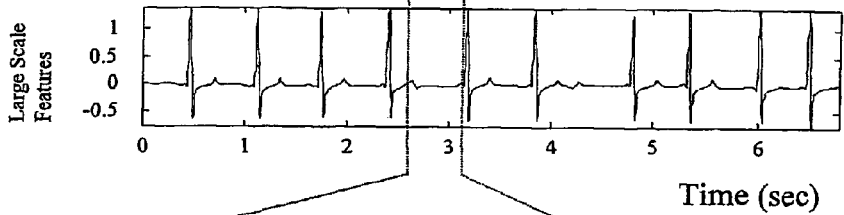
Figure 15:
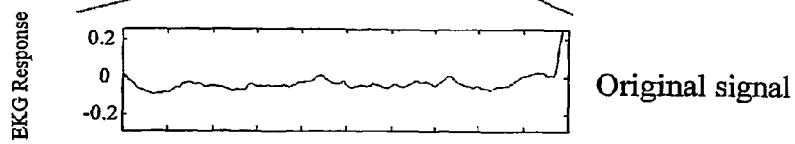
Figure 15:
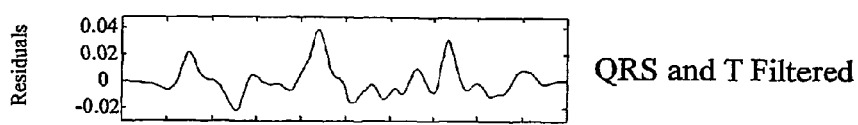
Figure 15:
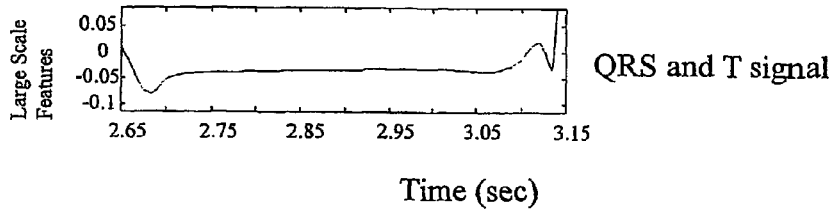

FIG. 15a shows a 2 second segment of EKG taken from a patient with atrial fibrillation (AF). FIG. 15b shows the wavelet scalogram plot associated with this EKG. FIG. 15c shows the corresponding modulus maxima of the scalogram of FIG. 15b.

FIG. 15d contains a 7 second segment of EKG exhibiting AF. FIG. 15e is a trace of EKG temporal components with small amplitude. FIG. 15f shows the larger magnitude components i.e. the QRS and T waves.

FIG. 15g is a plot of a two second 'blow up' of part of the signal of FIG. 15d; FIG. 15h is a plot of a two second 'blow up' of part of the signal of FIG. 15e; and FIG. 15i is a plot of a two second 'blow up' of part of the signal of FIG. 15f.

Referring to the Figures, the present method employs the use of a wavelet transform to analyse a cardiac signal.

The method involves the decomposition of the signal. This decomposition is accomplished by utilising wavelet transforms to decompose the signal in wavelet space.

A key distinction between the Fourier analysis of an EKG signal and its analysis by means of a wavelet function is that, whilst the Fourier transform employs a sinusoid function, a wavelet function is localised in time.

The methodology for such decomposition may include discretized continuous wavelet transforms, orthonormal wavelet transforms of decimated construction, non-decimated wavelet transforms, wavelet packet transforms and matching pursuit algorithms.

Signal processing employing wavelet transform analysis allows simultaneous elucidation of both spectral and temporal information carried within a signal. Such processing can employ either continuous or discrete transforms. The choice of wavelet transform used for a particular signal processing application depends on factors such as speed of computation necessary, the shape of signal specific features, the frequency resolution required, and the statistical analysis to be performed.

The preferred method employs the discretized continuous transform as it provides high resolution in wavelet space at lower frequencies.

This method thus employs the use of a discretized continuous wavelet transform to analyse a cardiac signal.

In particular, this method employs a wavelet transform as an interrogation tool for EKG signals of ventricular fibrillation.

A variety of wavelet functions are available, and the most appropriate is selected to analyse the signal to be investigated.

The wavelet transform of a continuous time signal, x(t), is defined as:

$$T(a,b) = \frac{1}{w(a)} \int_{-\infty}^{\infty} x(t) \bar{g}\left(\frac{t-b}{a}\right) dt \qquad \text{equation 1}$$

where g(t−b)/a) is the analysing wavelet function and '¯' denotes complex conjugate. w(a) is a scaling function usually of the form w(a)=$a^n$ where n is usually 1 or 0.5, and x(t), in this application, is the single channel surface EKG time signal. The transform coefficients T(a,b) are found for both specific locations on the signal, b, and for specific wavelet dilations, a. T(a,b) is plotted against a and b in either a surface or contour plot.

While other wavelet types may be employed the wavelets mainly used in this method are: the Mexican hat wavelet and the Morlet wavelet, examples of which are shown in FIG. 1.

The wavelet can translate along the signal (change in b) and dilate (change in a). This is shown schematically in FIG. 2 using a Mexican hat wavelet.

FIG. 3 illustrates the way in which a sinusoidal signal can be 'investigated' at various locations by Mexican hat wavelets of various sizes. The numerical value of the convolution (equation 1) depends upon both the location and dilation of the wavelet with respect to the signal.

FIG. 3a shows a wavelet of similar 'size' to the sinusoidal waves superimposed on the signal at a b location which produces a reasonable matching of the wavelet and signal locally. From the Figure it is apparent that there is a high correlation between the signal and wavelet at this a scale and b location. Here, the cross correlation of the signal with the wavelet produces a large positive number T(a,b).

FIGS. 3b and 3c show details of the wavelet transform of a signal using a wavelet of approximately the same shape and size as the signal in the vicinity of b. FIG. 3b shows a wavelet of similar scale to the sinusoidal waveform located at maximum negative correlation. This produces a large negative T(a,b) value. FIG. 3c shows a wavelet of similar scale to the sinusoidal waveform located at a position on the time axis where near zero values of T(a,b) are realised. FIG. 3d shows the effect on the transform of using the smaller a scale. It can be seen from the plot that the positive and negative parts of the wavelet are all in the vicinity of approximately the same part of the signal, producing a value of T(a,b) near zero. FIG. 3e shows that the same thing happens when using a much larger wavelet, since the wavelet transform now covers various positive and negative repeating parts of the signal, again producing a near zero value of T(a,b).

Figure 4:
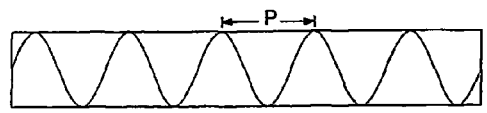

Wavelet transforms are not usually computed at arbitrary dilations for isolated locations in the signal, but rather over a range of a and b. A plot of T(a,b) versus a and b for sinusoidal data using the Mexican hat wavelet is shown in FIG. 4. Two methods are then employed to plot T(a,b), namely a contour plot or scalogram as shown in FIG. 4b, and a surface plot as shown in FIG. 4c. At small and large values of a, the near zero values of T(a,b) are evident from the plots, but at values of a of the order of one quarter of the wavelength of the sinusoid large undulations in T(a,b) correlate with the sinusoidal forms of the signal.

Figure 5:
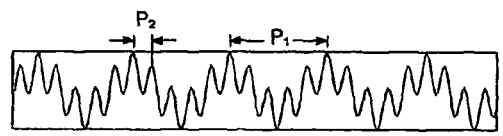
Figure 4:
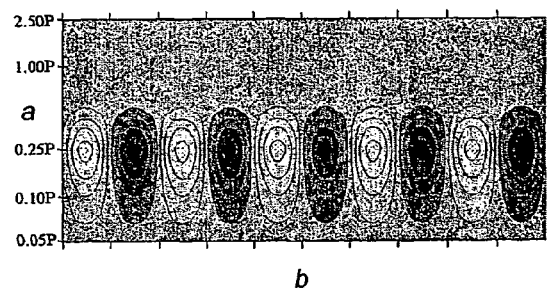
Figure 5:
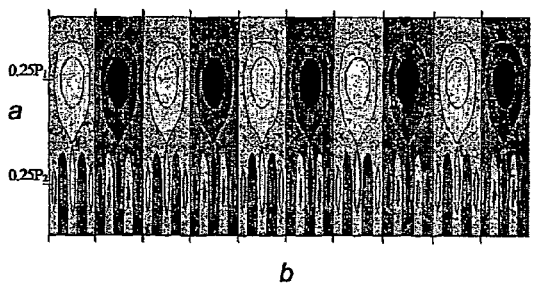
Figure 4:
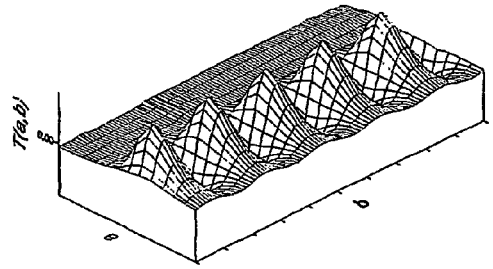
Figure 5:
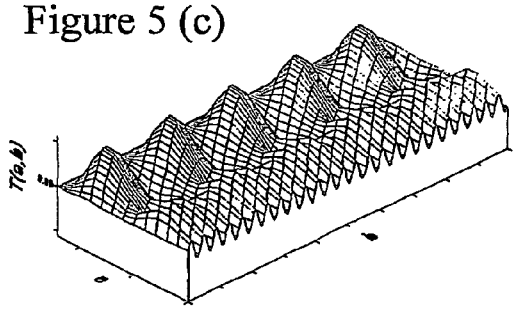

FIG. 5a shows two superpositioned sinusoidal waveforms, the first with period P1, the second with period P2. P1=5P2. FIGS. 5b and 5c, the transform plots of the superimposed waveforms clearly show the two periodic waveforms in the signal at scales of one quarter of each period. Thus, FIG. 5 clearly demonstrates the ability of the continuous wavelet transform to decompose the signal into its separate frequency components. That is, this transform 'unfolds' the signal to show its constituent waveforms.

The contribution to the signal energy at a specific a scale and b location is proportional to the two-dimensional wavelet energy density function which is, in turn, proportional to the modulus of T(a,b).

The method of the present invention thus involves the display of the transform as a contour plot. That is, the method is used to present information derived from an EKG trace of the heart in VF as a scalogram. The preferred form of presenting the information is as an energy scalogram, which presents the results as a plot showing the log of the wavelet energy coefficients, against the log of the bandpass centre frequency, $f_{bpc}$, of the wavelets for each time increment. The bandpass centre frequency is proportional to the reciprocal of the dilation value, a. This plot highlights small changes in amplitude over the scales of interest. The transform copes with repeating features in time with shifting phase, making it appropriate for real time applications such as this.

That is, by performing continuous wavelet transform analysis on the ECG in VF, and then by producing an energy scalogram of the results, it is possible to unfold the signal in such a way that a previously hidden structure is apparent, in contrast to the apparently disorganised VF signal.

The method then includes quantifying the wavelet decomposition. This wavelet decomposition provides both qualitative visual and measurable features of the EKG in wavelet space.

In practice, surface EKG tracings, recorded as soon as possible after the onset of VF, are analysed.

As a demonstration of the efficacy of the method, in an example of an experimental procedure utilising this method of analysis employing wavelet techniques, VF was induced in anaesthetised pigs via a pacemaker probe, using a 90V impulse at 60 Hz. All of the pigs remained in VF, untreated for a period of either 3 or 5 minutes. After this time, CPR commenced. The surface EKG (standard lead II) was recorded using needle electrodes. The EKG was sampled at 300 Hz using a 12-bit A to D converter. The method of the present invention was then performed using 32 EKG tracings recorded immediately after the onset of VF.

Figure 6:
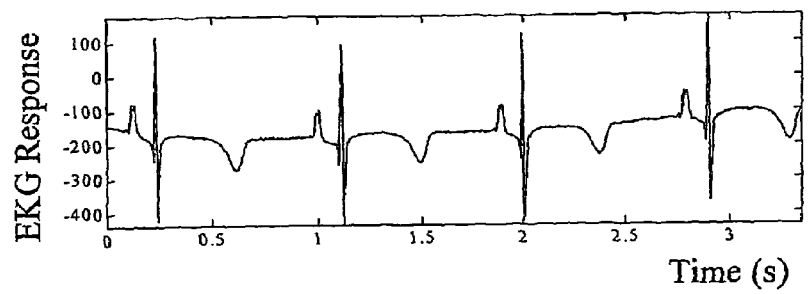
Figure 6:
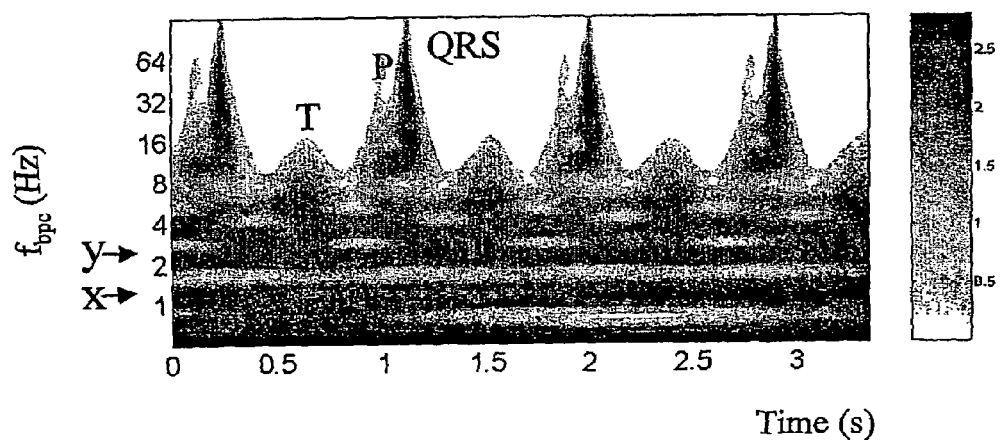
Figure 6:
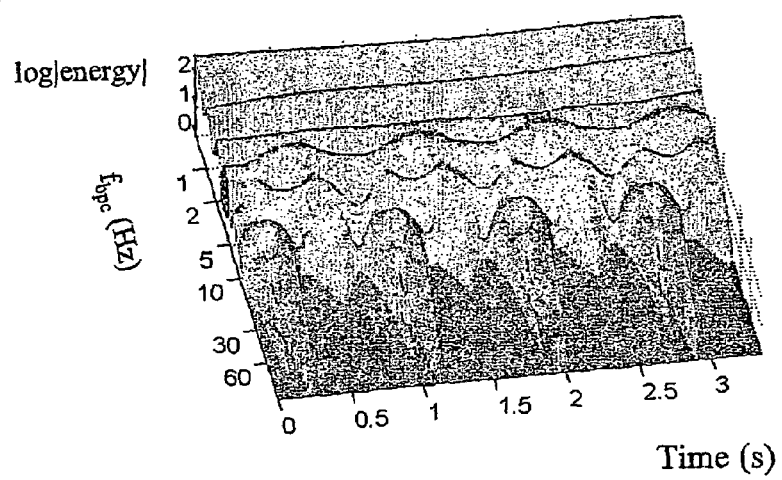
Figure 6:
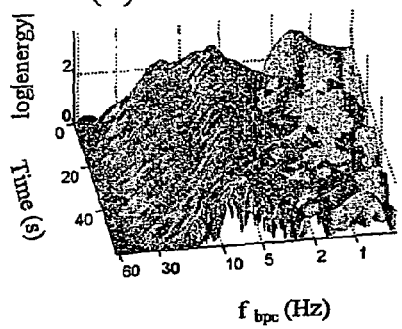
Figure 6:
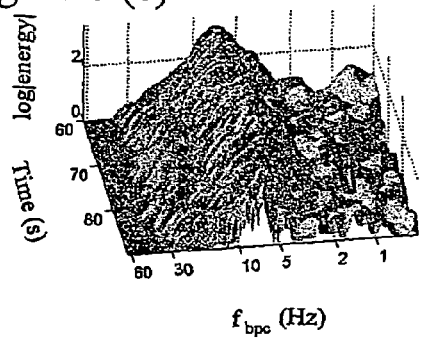
Figure 6:
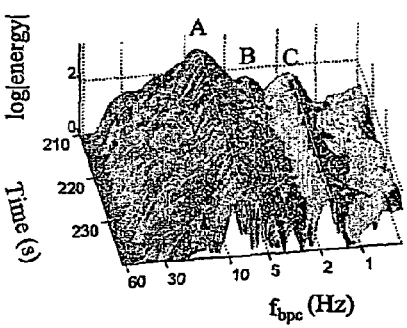
Figure 6:
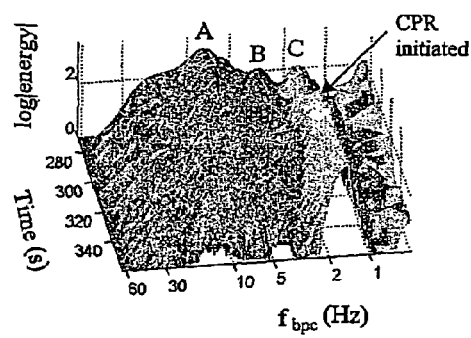

FIG. 6a represents 4 beats of a pig heart in sinus rhythm. FIGS. 6b and 6c shows the wavelet transform of the signal displayed in two and three dimensions respectively.

The QRS complex of the waveform is evident from the conical structures in FIG. 6b converging to the high frequency components of the RS spike. The P and T waves are also labelled in the plot. The 3D landscape plot of FIG. 6c shows the morphology of the signal in wavelet space. In FIGS. 6b and 6c the continuous horizontal band (X) is associated with a frequency of 1.7 Hz, the beat frequency of the sinus rhythm. The second band (Y) occurs at a frequency of approximately 5.1 Hz, corresponding to the separation of the P-QRS-T components in time. At higher frequencies the P, QRS and T components are individually resolved according to their frequency makeup and temporal location.

FIGS. 6d to 6g show the energy surfaces for four segments of EKG signal subsequent to the onset of VF, namely: (6d) 0–60 s; (6e) 60–100 s; (6f) 210–240 s; and (6g) 260–360 S.

The morphology of the VF signal in wavelet space can be seen from the Figures to contain underlying features within a more complex surface topography. The most significant features are the dominant ridges that appear in the transform surface through time.

FIG. 6f shows these ridges quite clearly. A high-energy ridge can be observed at around 10 Hz and two lower energy bands can be observed at lower frequencies. These three ridges are labelled A, B and C, respectively, in the plot. Other ridges are also present within the scalogram.

The energy surface in FIG. 6g contains the onset of CPR after 5 min of untreated VF. The institution of CPR is associated with a gradual increase in the passband frequencies of ridges A, B and C. This change in the composition of the VF signal reflects electrical changes in the fibrillating myocardium associated with the onset of CPR. This is because CPR produces antegrade myocardial blood flow and thus improves the metabolic state of the tissues, temporarily reversing the otherwise progressive decline in high band pass frequency components of the EKG wavelet decomposition.

FIG. 8a is a typical segment of an EKG trace of a pig heart in VF; FIGS. 8b, 8c, and 8d are the energy scalograms associated with the trace of FIG. 8a. As clearly illustrated by these diagrams the principle dilation (band pass centre frequency) component of the scalogram is approximately 10 Hz. However, using said method it is also apparent that this component is not constant. It 'pulses' with a degree of regularity. This structure is previously unreported.

FIG. 9 shows similar 'pulsing' in another porcine EKG signal. However, the structure is so pronounced that high energy, high frequency, intermittent components can be observed. These components have an occurrence frequency of the order of the original sinus rhythm: approximately 1.7 Hz.

FIG. 10a is a human EKG signal segment containing a shock event. FIG. 10b is the corresponding wavelet scalogram. It is apparent from the scalogram of FIG. 10b that both high frequency spiking and an intermittent high-energy region are present in the vicinity of 10 Hz and also above 10 Hz.

The high frequency spiking is unique to the method of the present invention and is not visible using conventional Fourier techniques. The rich structure made visible within the EKG by the wavelet transform method is evident in the scalogram.

It is clearly seen from the Figures that applying the wavelet transform to an EKG signal of VF demonstrates that this signal is a rich source of valuable information. That is, it produces a display showing real time visualisation of the distribution of energies and coherent structures within the signal for use by a clinician in the selection of treatment strategies.

Using this method of analysis it is feasible to obtain real-time visual display of the EKG frequency characteristics in the wavelet domain during resuscitation. The scalogram produced provides information about the myocardium that is not available from a standard single channel surface EKG.

The wavelet scalogram decomposition can be displayed as a real time scrolling window, as shown in FIG. 9. This window is useful as an aid for clinical decision making. It can be used as a stand-alone tool, or as basis for on-line statistical analysis of the current state of a heart.

To produce the window, a MATLAB™ R11 application is used. Each EKG sample taken results in the updating of a FIFO (First In First Out) buffer, and the EKG plot of FIG. 9a. The scalogram of FIG. 9b is then shifted to the right and clipped before the 'missing' new right hand data is calculated, using conventional matrix algebra, and filled.

This results in the two scrolling windows of FIG. 9. The exponential ramp in the bottom right corner shows the compact support of the wavelet utilised at the given scale.

Higher resolution scalograms are achieved through implementation on higher specification machines, purpose built hardware, or application specific software with coding using a lower level programming language, such as C++.

CPR produces artefacts in the EKG signal. Additionally, this method delivers information the value of which is not degraded once the CPR artefacts are filtered from the EKG signal.

From examination of the scalograms shown in FIGS. 6g, 7a and 7b it can be seen that the VF signature and the signature of the CPR artefacts occupy distinct areas of the scalogram, which permits their separation.

Known techniques such as the Modulus maxima method are now available to reduce the non-zero data points in the wavelet scalogram. This method reduces the topography of the scalogram surface to a series of ridges, thereby considerably reducing the amount of data required to represent the signal in the wavelet space.

The modulus maxima obtained from a bandlimited signal with a wavelet of finite compact support in the frequency domain defines a complete and stable signal representation.

In this method, temporal filtering of the original EKG signal to disassociate the CPR signature from the heart signal can either be done directly, using the wavelet energy scalograms, or indirectly through modulus maxima techniques. This allows the heart to be monitored without necessitating cessation of CPR to allow rhythm recognition.

Further to the above, the method may also be applied to patients suffering form atrial fibrillation (AF) as a means of disassociating the prevalent QRS and T waves from the remainder of the signal.

Wavelet decomposition of the ECG signal is performed using an appropriate wavelet function. The modulus maxima technique is used to encapsulate the scalogram information in a series of ridges. Filtering of the signal is then undertaken using the modulus maxima information and through reconstruction the clinically useful information is isolated from the signal.

Specifically, FIG. 15a shows the wavelet transform decomposition of a 2 second segment of ECG taken from a patient with atrial fibrillation. Below the ECG trace is a wavelet scalogram plot. The corresponding modulus maxima of the scalogram is plotted below the scalogram.

For example, FIG. 15d contains a 7 second segment of ECG exhibiting AF. The signal has been partitioned using a modulus maxima ridge following algorithm. The modulus maxima ridges have been separated into large and small scale features by thresholding the signal at a predetermined wavelet scale. A blow up of part of the signal is given in the lower three plots in the figure: FIGS. 15g, 15h and 15i. The middle of these plots contains the partitioned signal with the QRS complex and T wave filtered out revealing regular, coherent features that appear at a frequency of approximately 400 beats per minute, typical of AF. The lower plot contains the partition with the filtered out QRS and T waves. Although, a relatively simple modulus maxima technique was used in this pilot study whereby the modulus maxima lines were simple partitioned into two subsets, the ability of the technique to separate the signal into QRS and T waves and underlying atrial activity is evident from the results. It is known that the decay in amplitude of a modulus maxima corresponding to a signal feature can be a function of the scale of the wavelet. It is possible to use this property to separate the ridge coefficients into a noisy and coherent part. In this way, further differentiation of the modulus maxima information can be implemented within a more sophisticated algorithm. This will facilitate the further separation of background noise, QRS and T waves, and atrial activity.

This method thus facilitates useful interpretation of previously unintelligible EKG signals.

In patients presenting with uncoordinated rapid electric activity of the ventricle of heart, known as ventricular fibrillation (VF), there is no effective pulse and myocardial blood flow ceases. Even the institution of optimal cardiopulmonary resuscitation (CPR) of the patient does not achieve more than 30% of the normal cardiac output. Ischaemia during cardiac arrest leads to a rapid depletion of myocardial high-energy phosphates, deterioration of transmembrane potentials, and disruption of intracellular calcium balance. Paradoxically, the myocardium in VF has supranormal metabolic demands. For this reason resuscitation attempts become less likely to succeed with the passage of time, and electrical defibrillating shocks increasingly result in asystole or EMD.

After prolonged cardiac arrest, the use of pharmacological measures or CPR before attempting defibrillation may increase the chances of successful resuscitation. This invention provides a robust and reliable method of analysis of the state of the myocardium in VF that prevents attempts to defibrillate at times that are unlikely to be successful, or even harmful to the heart. This method also provides an indication of the best way in which to optimise the metabolic state of the heart prior to counter-shock.

The method includes steps to establish a standard against which to evaluate collected data in a particular incidence.

The method further employs use of measurable signal characteristics derived from the position and amplitude of features in the scalogram to estimate both the condition of the myocardium, and downtime of the subject while in VF.

The method thus provides for optimal treatment of the heart in VF, so fulfilling specific patient needs, by therapeutic intervention, if appropriate.

Figure 7:
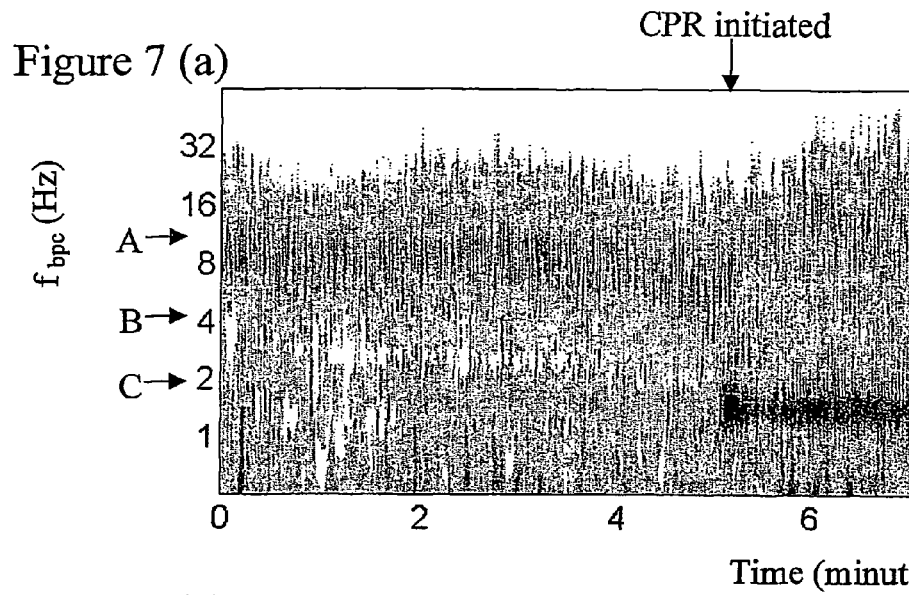
Figure 7:
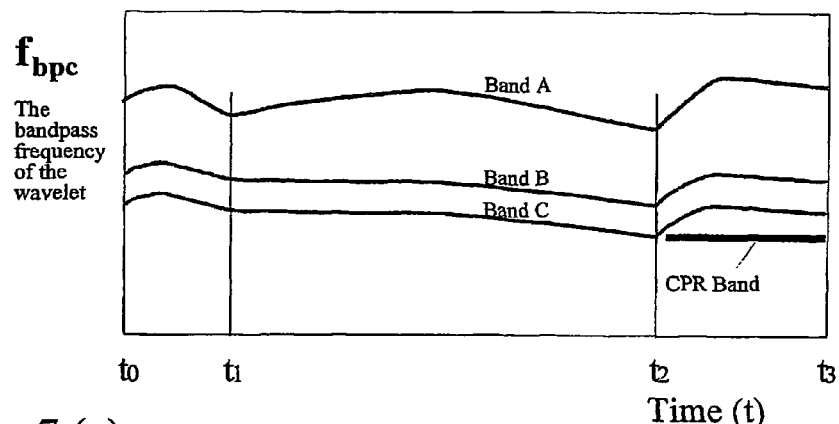
Figure 7:
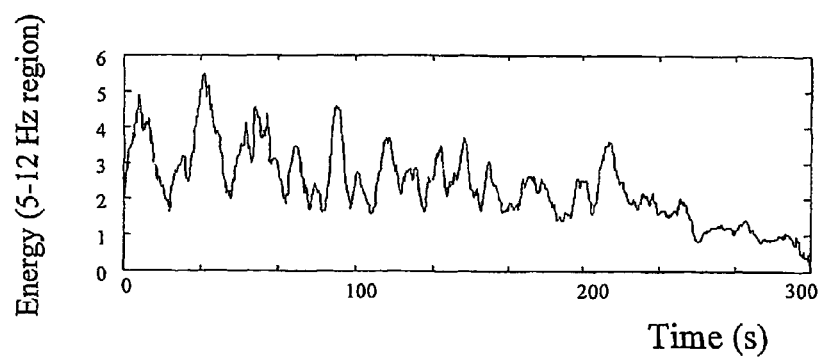

An energy scalogram such as that shown in FIG. 7 displays three distinct bands, labelled A, B, C. It is possible to derive quantifiable measures using correlations between the location and energy content of the bands.

Band A of FIG. 7b represents the dominant energy band seen in the scalogram of FIG. 7a, and corresponds to the tachycardic beating of VF. However the scalogram is much more informative in that it also shows, as bands B and C, the behaviour of other frequency components of the signal which were previously unreported.

FIG. 7a shows a 2D energy scalogram. It includes the first 5 minute period of VF, followed by a 2.5 minute period of CPR. The onset of CPR is clearly identified by the distinct horizontal dark band in the lower right quadrant of the Figure. Over the first 5 minute period, three bands, labelled A, B, C, can be clearly seen in the scalograms. These bands correspond to the ridges of FIGS. 6d to g. The increase in the frequency components of these three bands after the onset of CPR is evident in the plot. Bands 1 and C follow trajectories similar to each other in the scalogram, reducing in frequency over time. Band A, however, moves independently of the other two. Initially Band A increases, then it decreases to a local minimum value at approximately 70 s. Between 70 and 160 s it increases relative to Bands B and C. Finally, it decreases until the start of CPR after 300 s. The same pattern was present in all 32 pig EKG traces of the experiment.

Obvious increases in the passband frequency of all three bands are observed in the scalogram after the onset of CPR. For some of the signals studied this increase in band C is masked by the dominant CPR band, and thus cannot be seen in the scalogram.

FIG. 7b provides a schematic diagram of the salient features contained within the scalogram plots, where to is immediately after the onset of VF; t2 is the start of CPR; and t3 is the end of the analysis. FIG. 7c shows the relative proportion of energy contained in the scalogram in the 5 to 12 Hz region through time. There is an obvious decay in the relative energy associated with this region which is associated with the breakdown of coordinated activity in the heart.

The steps of the method of the present invention described above establish that during the course of VF there is a reduction in the proportion of energy within the dominant frequency band indicated in FIG. 7c. This dominant frequency band, Band A in FIG. 7a, is demonstrated to be approximately 10 Hz for pig VF.

The energy within this band changes rapidly. This is illustrated by the 'pulses' in FIGS. 8,9,10.

The FIGS. 6,7,8,9,10 show that applying the wavelet transform to an EKG signal of VF demonstrates that this signal is a rich source of valuable information.

The underlying hypothesis of the method of the present invention is that the scalogram associated with an EKG correlates to the state of the myocardium as it decays subsequent to the onset of VF.

The method uses the information contained in the energy scalogram associated with an EKG to predict the likely success of clinical intervention, namely shocking.

It is therefore possible to develop a wavelet transform based tool for the prediction of shock outcome during ventricular fibrillation by:

1. collecting and collating data from sets of archived EKGs recorded from humans in VF where attempts to resuscitate by shocking were made; and
2. developing a classifier for reference purposes.

Figure 11:
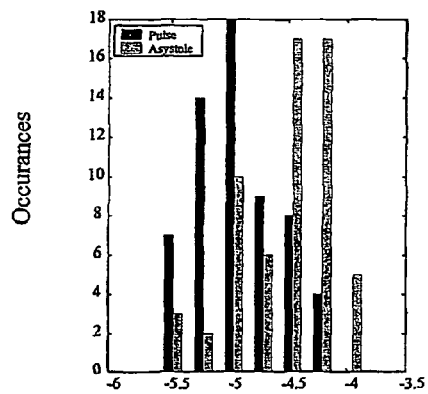
Figure 11:
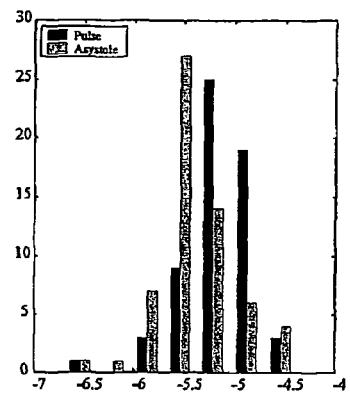

FIG. 11 is a classification of the shock outcome in either asystole or a rhythmic response using a relatively simple statistical analysis. The experiment yielding the results to compile these Figures involved use of the lead II outputs of standard three lead EKGs of 120 patients in VF. Each trace is of three second duration sampled at 100 Hz. Of these patients, 60 returned to sinus rhythm while the other 60 deteriorated to asystole, post shock.

Each trace was decomposed into an associated wavelet transform from which its energy scalogram was generated. The volume under this surface was then normalised to render the results independent of signal amplitude, but instead the result of the relative wavelet constituents of the signals. The log of the mean values at each dilation (band centre frequency) for each was then recorded. FIGS. 11a and 11b show the distribution of energies in a lower frequency band (1.9 Hz) and at the 9.3 Hz band. Clearly, through visual inspection, it is apparent that the proportion of energies around the 10 Hz band is higher for successful defibrillation attempts.

The method then extends to apply neural techniques to analysis of wavelet pre-processed EKG signals.

A pilot study conducted to determine the feasibility of using artificial neural techniques to provide a tool to predict the outcome of defibrillation during VF used eight human EKG trace segments containing shock events.

In these cases, the result of shocking was unequivocal—four patients returned to VF, and four experienced return of spontaneous circulation (ROSC).

The traces were transformed using the Morlet wavelet, and energy scalograms containing thirty frequency levels were produced. This was then split into eight overlapping sections as shown in FIG. 12a, each of 200 points (2/3 seconds duration). These 200 location points were sub-sampled down to 50 to give eight scalograms for each trace of 50×30 elements. The volume under the energy scalograms were normalised and the patterns fed into a 'winner take all' Kohonen network with two output units and built in conscience (to avoid local minima). That is, the network was asked to group the 64 input patterns into two classes. All but ten outputs were collectively classified correctly giving a mean pattern error of 0.156 (against 0.5 average pattern error expected from random inputs).

Since this is a vector quantisation method (VQM) it was possible to identify how the network differentiates the patterns through inspection of its connective weights. The weights from each location position across all scales in the network are approximately the same, which means that there are no markers with which to synchronise the different pre-processed traces. This confirms that this neural network is too simple for this purpose. That is the network is not equipped to 'consider' the relative phase of each input pattern. FIG. 12b shows the weights for the 'success' (ROSC) and 'failure' (VF) to the output units from the first two time slices across all scales. The weights indicate the classes are differentiated by the proportion of energy in the lower scales, which can be seen when compared with FIG. 11.

Although the above described method indicates the slight drop in the dominant frequency expected, the drop is very marginal which leads to the conclusion of the lack of competence of previously proposed methods as a defibrillation success predictor.

In summary, a library of human ECG data containing data sets of human VF with attempts to resuscitate by shocking is used as a database. This database is extended to include data sets containing various methods of shocking including, for example, biphasic shocking. The biphasic shock waveform has resulted in an increased proportion of successful defibrillation attempts and is set to become the standard treatment for cases of VF.

In one example, the recognised outcomes are defined by trace components of the post-shock window lasting until next shock (if present). If the ratio of the given rhythm exceeds 10% of the total window length the rhythms are prioritised according to the sequence:

| Class | Rhythm | Ratio |
|---|---|---|
| 1 | Pulse (SVR) | +10% |
| 2 | No pulse (EMD) | +10% |
| 3 | Isoelectric (Asystole) | +10% |
| 4 | VF | +10% |

Class 5 is the class of VF preceding shocks where VF re-establishes itself within 5 seconds following the shock (i.e. no change). The VF in all the other classes were non-VF in this period.

Wavelet analysis of this information in accordance with the method of the invention is then performed to:

construct a wavelet visualisation of the signal—usually by plotting wavelet energy surfaces against the location parameter b and the inverse of the dilation parameter a;

provide measurable characteristics of the signal for estimation of downtime of the patient;

provide measurable characteristics of the signal for determining the health of the heart post CPR; and to construct energy scalogram devised for the method—which uses the energy density function and the reciprocal of the wavelet a scale for use as a predictor tool.

As described above it is possible to use artificial neural network based techniques to develop such an indication of the state of myocardium. In the alternative, it is possible to classify the wavelet scalogram through multilayered feed-forward network types.

The method may include the development of a modulus maxima algorithm tool for the preprocessing of ECG prior to its input into a neural network classifier.

Using this technique improves network performance whether this data is further encoded, or presented as a whole, larger, sparse matrix as a pattern in the input space.

This method therefore utilises the generalisation properties of a feed forward multi-layer network to predict the likelihood of defibrillation success from the wavelet transform of the EKG traces. This multi-layer network with its relatively simple dynamics, when combined with wavelet pre-processing, has proved itself a useful tool as a universal approximator.

The classes of multi-layer network types of use in this method are:

Multi-layered feed forward (MLFF) neural networks with back propagation training and monotonic activation functions; and Radial Basis Neural Networks (RBNN) as have previously been successfully applied to the denoising of medical Doppler ultrasound signals with wavelet preprocessing.

As described above, the method involves the decomposition of EKG signals into a complete basis set defined by the wavelet shape and other parameters by salient basis functions of a different basis set, converged upon through regression techniques (sigmoid in the case of multilayer neural networks, Radial basis etc).

These regression techniques can also be used to construct a wavelet basis function set directly.

Methodologies for restricting the search space of the wavelet basis functions considered are known. Whilst this wavelet network has been shown to be effective for chaotic time series prediction, its implementation involves the use of wavelet frames of a decimated, dyadic, construction. The method of the present invention may employ continuous wavelet networks spanning a redundant wavelet basis which, although computationally more expensive, overcomes the time invariance constraint and the limited size of input space associated with use of wavelet frames.

The method may use conventional gradient decent methods to produce a single layer wavelet classifier.

These wavelet networks may be further employed as part of a multilayer system as a non-parameterised estimate of the original trace for input to further hidden layers.

The network type of choice for the automated prediction system of the method is selected on the basis of its sensitivity and selectivity in correctly classifying successful defibrillation outcomes in test set data, since this is most clinically useful.

Thus experimental comparison of the three techniques demonstrates the efficacy of the wavelet transform technique.

The nature of underlying atrial activity can also be determined from wavelet decomposition of the EKG signal. The wavelet function gives information regarding the amplitude and, where appropriate, phase of the transformed signal. It is known that pressure readings taken from the aorta correlate to forms of atrial activity within the heart. Areas of localised high energy contained within the scalogram can be demonstrated to correlate with these pressure readings. This experimental result is extrapolated to mean that areas of localised high energy contained within the scalogram correlate with forms of atrial activity within the heart.

FIG. 13a shows the aorta pressure, FIG. 13b the EKG trace, for the same time period as FIG. 13a, and FIG. 13c shows the scalogram for the EKG of FIG. 13b. It is apparent that there is an increase in energy in the system during an atrial pulse, indicated by the dark blotches occurring in the scalogram at an $f_{bpc}$ of around 10 Hz. There is a frequency component between 1 and 2 Hz. As shown in FIG. 13d, which highlights the phase of the scalogram between 1 and 2 Hz, it is apparent hat the lines of zero phase are in alignment with the atrial pulse.

In a further scalogram, shown in FIG. 13e, produced by using the Mexican hat wavelet transform which is real and has better temporal resolution, but worse frequency resolution than the complex scalogram of FIG. 13c, it is demonstrated that positive high amplitude components are shown at the same positions for scales of between 1 and 2 Hz, thus reinforcing the findings extrapolated from FIG. 13c. That is as shown in FIG. 13f, the lines of zero phase correlate with the pulse position.

The lines of zero phase within the 1.8 Hz frequency band also align with regular peaks in the scalograms, as shown in FIGS. 14a, 14b & 14c. This links the presence of the 1.8 Hz band with the observed peaks at higher frequencies. This correlation between the 1.8 Hz band and the aorta pressure pulse suggests atrial activity is present.

In a further application of the method, means for identifying the optimum timing for application of the defibrillation shock can be extrapolated from the pulsing identified by the wavelet technique and shown in FIGS. 8, 9, 10, and 14, by comparison with traces of attempts at defibrillation which initially fail but are subsequently successful.

Thus, any data sets, in the above, that correspond to multiple shocking of the same patient, where defibrillation has been repeatedly attempted are considered separately since these traces hold important information.

The pilot study detailed above used Morlet wavelet based energy scalogram decomposition of signal segments immediately prior to shocking. A full parametric wavelet study of the method determines the optimum method.

The method includes the development of a classifier using the wavelet transform analysis.

Various types of neural network classifier are achievable using this method.

The linkage of shock timing to the phase information of wavelet components allows for increased defibrillation success and reduced shock energies. The wavelet-derived information can also be employed to predict the likelihood of shock success, preventing futile or harmful defibrillation attempts, and providing a predictor of an optimal resuscitation strategy or strategies.

This method demonstrates the utility of the wavelet transform as a new method of EKG signal analysis during VF. It provides a robust, real-time solution to the problem of useful monitoring of the myocardium during resuscitation.

When compared with conventional statistical methods, such as fast Fourier transforms, it is seen that the temporal resolution of the wavelet technique gives a scalogram which better describes the non-stationary, intermittent, nature of the EKG trace to be analysed, and gives a method of greater predictive effectiveness than is already known. The effectiveness criteria for the networks of the method of the present invention are based upon their sensitivity and selectivity in correctly classifying successful defibrillation outcomes from test data sets.

Although this description refers to wavelet transform analysis, this term is to be construed to include matching pursuit algorithms and similar analysis techniques.

Modifications and improvements can be made to the above without departing from the scope of the invention.

The invention claimed is:

1. A method of decomposition of waveforms in a cardiac signal comprising the steps of:
   a) connecting electrodes to a patient whose heart is in Ventricular Fibrillation (VF);
   b) deriving analogue input signals from the electrodes;
   c) sampling said analogue input signals to derive the cardiac signal (EKG);
   d) digitising said EKG signal;
   e) employing wavelet transform analysis to process said digitised EKG signal;
   f) extracting key features from the wavelet transform representation to predict the outcome of a specific interim therapeutic intervention during the Ventricular Fibrillation; and
   g) guiding a resuscitation protocol based on the prediction, said guidance comprising the steps of;
   h) using an analytical method to determine the likely outcome of a defibrillation shock; and i) determining whether to provide at least one interim therapeutic intervention from a group comprising defibrillatory shock, CPR and pharmaceutical, before shocking.

2. The method of claim 1, wherein the analytical method is characterised by learning vector quantisation (LVQ) methods, for example Kohonen Networks.

3. The method of claim 1, where the analytical method is characterised by statistical, stochastic methods, for example Baysian Methods.

4. The method of claim 1, where the analytical method is characterised by multi-layered neural network methods, for example Radial Basis Neural Networks.

5. A method of decomposition of waveforms in a cardiac signal comprising the steps of:
   a) connecting electrodes to a presenting patient whose heart is in Ventricular Fibrillation (VF) after the commencement of Cardio-Pulmonary Resuscitation (CPR);
   b) deriving analogue input signals from the electrodes;
   c) sampling the analogue input signals to derive the cardiac signal (EKG);
   d) digitising said EKG signal;
   e) employing wavelet transform analysis to process said digitised EKG signal; and
   f) extracting key features from the wavelet transform representation to predict the outcome of a specific interim therapeutic intervention during the Ventricular Fibrillation.

6. The method of claim 5, further comprising the steps of:
   a) filtering said cardiac signal such that the CPR component is disassociated/separated from the heart signal;
   b) producing an energy wavelet scalogram; and
   c) temporally filtering the scalogram using ridge following techniques.

7. The method of claim 6, wherein said ridge following techniques are characterised by modulus maxima techniques.

8. The method of claim 6, further comprising the steps for guiding resuscitation protocol of:
   a) using an analytical method for determining the likely outcome of a defibrillation shock; and
   b) determining whether to provide at least one interim therapeutic intervention from a group comprising immediate defibrillatory shock and CPR, before shocking.

9. The method of claim 8, wherein said analytical method is characterised by learning vector quantisation (LVQ) methods, for example Kohonen Networks.

10. The method of claim 8, wherein said analytical method is characterised by statistical, stochastic methods, for example Baysian Methods.

11. The method of claim 8, wherein said analytical method is characterised by multi-layered neural network methods, for example Radial Basis Neural Networks.

12. A method of decomposition of waveforms in a cardiac signal comprising the steps of:
   a) connecting electrodes to a presenting patient whose heart is in Atrial Fibrillation (AF);
   b) deriving analogue signals from said electrodes;
   c) sampling the analogue input signals to derive the cardiac signal (EKG);
   d) digitising said EKG signal; and
   e) employing wavelet transform analysis to process said digitised EKG signal; and
   f) extracting key features from the wavelet transform representation to predict the outcome of a specific interim therapeutic intervention during the Atrial Fibrillation.

13. The method of claim 12, further comprising the step of filtering said cardiac signal such that the QRS complex and T components are disassociated/separated from the heart signal, comprising:
   a) producing an energy wavelet scalogram; and
   b) temporally filtering the scalogram using ridge following techniques.

14. The method of claim 13, wherein said ridge following techniques are characterised by modulus maxima techniques.

15. The method of claim 13, further comprising the step for guiding the course of therapeutic intervention taken, comprising:
   a) using an analytical method for determining the likely outcome of a cardioversion shock; and
   b) determining whether to at least one therapeutic intervention from a group comprising cardioversion shock, and drug therapy.

16. The method of claim 15, wherein said analytical method is characterised by learning vector quantisation (LVQ) methods, for example Kohonen Networks.

17. The method of claim 15, wherein said analytical method is characterised by statistical, stochastic methods, for example Baysian Methods.

18. The method of claim 15, wherein said analytical method is characterised by multi-layered neural network methods, for example Radial Basis Neural Networks.

* * * * *